United States Patent [19]
Kotwica

[11] Patent Number: 4,659,433
[45] Date of Patent: Apr. 21, 1987

[54] CONCENTRATING AND DEHYDRATING APPARATUS FOR MALEIC ANHYDRIDE

[75] Inventor: Roland Kotwica, Pont-Sainte-Maxence, France

[73] Assignee: Societe Chimiques des Charbonnages, Paris, France

[21] Appl. No.: 522,772

[22] Filed: Aug. 12, 1983

Related U.S. Application Data

[62] Division of Ser. No. 272,819, Jun. 11, 1981, Pat. No. 4,414,398.

[30] Foreign Application Priority Data

Jun. 13, 1980 [FR] France ............... 80 13117

[51] Int. Cl.$^4$ .......................................... B01D 3/02
[52] U.S. Cl. .................................. 202/173; 202/183; 202/186; 202/236; 203/42; 203/87; 159/13.2
[58] Field of Search ............ 159/13 A, 13 C, 13 B, 159/49; 202/183, 186, 236, 173; 203/42, 87

[56] References Cited

U.S. PATENT DOCUMENTS

| | | | |
|---|---|---|---|
| 3,203,466 | 8/1965 | Eckstrom | 159/13 A |
| 3,265,115 | 8/1966 | Maier | 159/13 A |
| 3,273,630 | 9/1966 | Kühnlein | 159/13 A |
| 3,356,125 | 12/1967 | Standiford, Jr. | 159/13 A |
| 3,450,603 | 6/1969 | Meyers et al. | 159/13 C |
| 3,476,775 | 11/1969 | Sueur | 203/87 |
| 3,993,671 | 11/1976 | Ramioulle | 260/346.8 M |
| 4,233,267 | 11/1980 | Coker et al. | 202/186 |

FOREIGN PATENT DOCUMENTS 1928207 12/1970 Fed. Rep. of Germany .
737391 9/1955 United Kingdom .

Primary Examiner—David L. Lacey
Attorney, Agent, or Firm—Millen & White

[57] ABSTRACT

Apparatus for concentrating and dehydrating maleic acid to form maleic anhydride, comprising: at least a first and a second vertical, independent and distinct, falling thin-film, multitubular evaporators of the static type arranged in series, wherein the first thin-film multitubular evaporator of the static type has an upper part and a lower part and includes a feedpipe at the upper part and a discharge pipe at the lower part; a separator connected by its sidewall to the discharge pipe from the first evaporator and including a first discharge pipe at the upper portion thereof and a second discharge pipe at the lower part; the second thin-film multitubular evaporator of the static type having a feedpipe having an upper part and a lower part connected to the second discharge pipe from the separator and including a discharge pipe only at the lower part thereof; a boiler having an upper part and a lower part, said upper part of said boiler being connected to and in open communication with the lower portion of the second evaporator, said boiler being further in communication with a first discharge pipe for liquid at the lower part of the boiler and a second discharge pipe at the upper part of the boiler; a scrubber; a condenser having a pipe for discharge of the condensates, said condenser being serially connected between the second discharge pipe from the boiler and the scrubber; and a recycle pipe connecting the discharge pipe from the condenser with the second discharge pipe from the separator.

4 Claims, 1 Drawing Figure

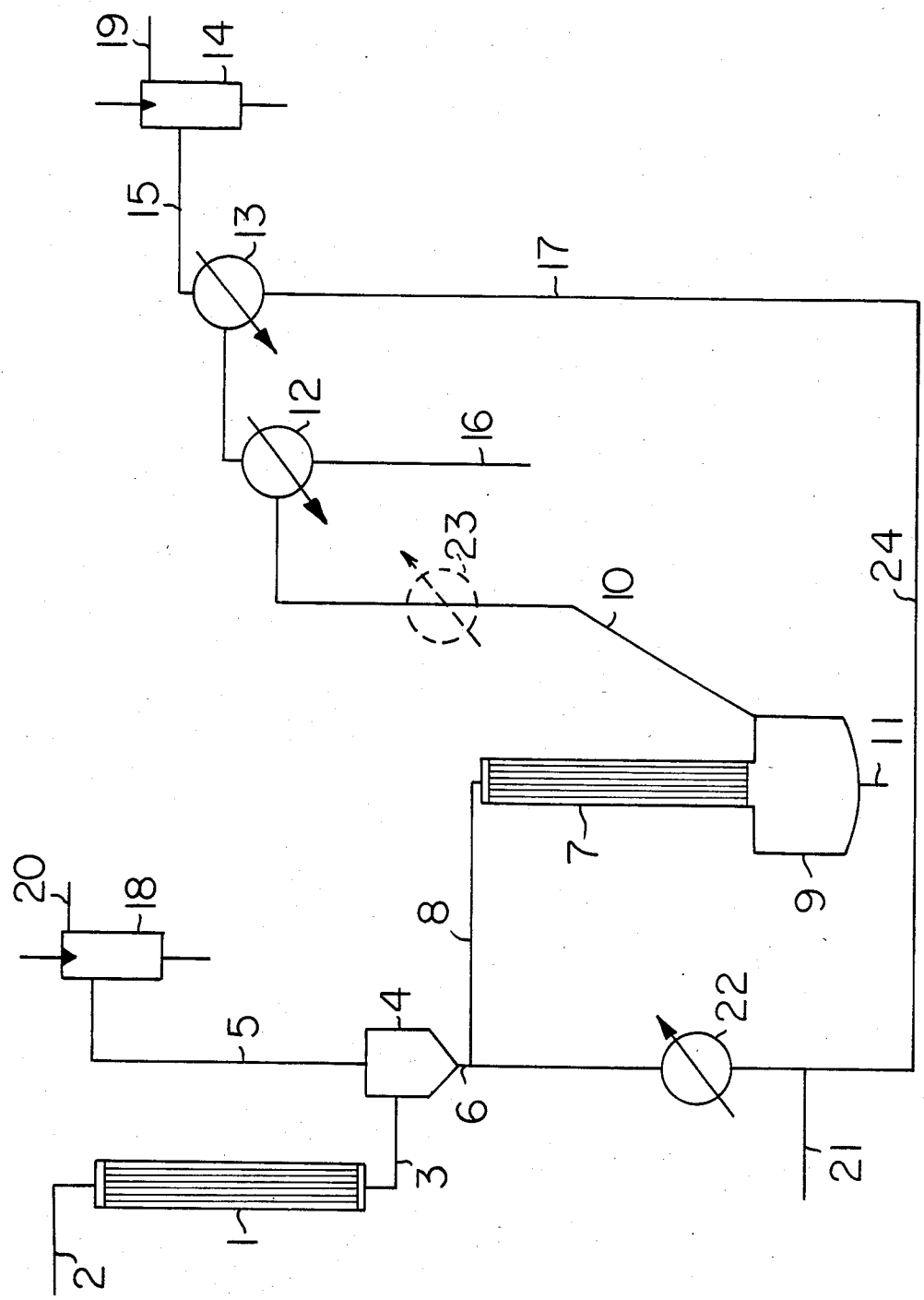

CONCENTRATING AND DEHYDRATING APPARATUS FOR MALEIC ANHYDRIDE

BACKGROUND OF THE INVENTION

This is a division of application Ser. No. 272,819, filed June 11, 1981, now U.S. Pat. No. 4,414,398, issued Nov. 8, 1983.

This invention relates to the production of maleic anhydride and in particular to an improved process and apparatus pertinent to the stage of the dehydration of maleic acid.

The synthesis of maleic anhydride by the oxidation of benzene or $C_4$ hydrocarbons (butane, butenes, butadiene, or $C_4$ cuts resulting from the vapor-phase cracking of petroleum cuts) leads to a product containing deleterious impurities. One of the best known methods of eliminating these impurities involves the washing of the oxidation product with water in order to convert it at least partially into maleic acid and then subjecting the resultant solution to dehydration to form maleic anhydride.

For the dehydration step, French Pat. No. 2 062 821 describes the dehydration of maleic acid into maleic anhydride in two stages: (A) concentrating a solution of maleic acid having a content from 30 to 50% by weight up to more than 90% in at least one agitated thin-film evaporator; and (B) dehydrating the concentrated solution of maleic acid into maleic anhydride while simultaneously eliminating the impurities, the main impurities being fumaric acid. Likewise, in French Pat. Nos. 1 524 319 and 2 242 388, countercurrent agitated thin-film evaporators are employed. The reason why these particular evaporators are employed is high heat transfer coefficient, short residence time, liquid film wiping and limitation of liquid entrainment by the effect of the reactor.

Conversely, the employment of these countercurrent agitated thin-film evaporators causes difficulties because of their mechanical complexity. The moving rotor results in vibrations, requires additional energy consumption and necessitates the employment of lubricating oil and cooling liquid for the bearings. Also, a simple motor failure or seizing of the rotor leads to stoppage of the whole plant. Finally, owing to mechanical restraints of these apparatus, they are limited in evaporation area and in the magnitude of the heat exchange coefficient, consequently limiting the productive capacity of the plant.

In a different evaporation technique, British Pat. No. 737 391 describes the concentration and dehydration of a solution of maleic acid in a battery of three single-tube horizontal evaporators which operate cocurrently and are mounted in series.

SUMMARY OF THE INVENTION

An object of this invention is to provide an improved evaporation system in the conversion of maleic acid to maleic anhydride.

In addition to a new process, another object is to provide apparatus for conducting said process.

Upon further study of the specification and appended claims, further objects and advantages of this invention will become apparent to those skilled in the art.

To attain these objects, one aspect of this invention resides in the employment of thin-film static tubular evaporators operating cocurrently, the liquid phase being distributed over the wall of the evaporator and the gaseous phase flowing in the same direction being concentrated axially. These thin-film static tubular evaporators are also described in the gravity mode as falling film evaporators. See the article "Evaporation" in Chemical Engineering, Volume 60, April 1953, pages 227–230, and the Chemical Engineers Handbook, Perry and Chilton, 5th Edition, pages 11-29 and 11-30.

According to a more comprehensive aspect, the present invention is a continuous method of dehydration of maleic acid into maleic anhydride, comprising a first stage of concentration of an aqueous solution of maleic acid and a second stage of dehydration of the concentrated maleic acid into maleic anhydride, the concentrated acid entering the second stage having maleic anhydride added to it, and wherein each of the two stages is effected in at least one thin-film static tubular evaporator operated cocurrently with respect to liquid and vapor.

The thickness of the thin-film inside the evaporator tubes decreases during evaporation, but is generally of a thickness of preferably 0.05 to 2.5 mm.

The concentrated acid entering the second stage has preferably added to it from 15 to 35 parts by weight of maleic anhydride per 10 parts by weight of concentrated acid. In this way, conversion into fumaric acid is reduced by dilution of the concentrated maleic acid, so additional loss in yield and plugging of the piping are avoided.

The aqueous solution of maleic acid entering the first stage may be at any concentration. Advantageously, it will be close to saturation concentration at the temperature at which the solution is held. Thus, it is preferable to employ solutions titrating between 30 and 50% by weight of maleic acid, held at temperatures lying respectively between 15° and 40° C.

This feed solution is concentrated in the first stage by evaporation in a thin-film static tubular evaporator cocurrently, preferably a multitubular evaporator, at a temperature of preferably between 120° and 140° C., preferably at a pressure reduced to a value between 200 and 500 mm of mercury, with a residence time preferably between 1 and 60 seconds. In any case, it is preferred that the conditions are such that the concentrated solution collected in the separator connected to the evaporator has a concentration of maleic acid of between 85 and 95%. Otherwise, it has in fact been found that at a concentration higher than 95%, a significant deleterious amount of fumaric acid is present.

The resultant concentrated solution withdrawn from the concentration evaporator is collected in a separator wherein the water vapor phase is exhausted through the top end. A scrubber removes a substantial percentage of the small amounts of maleic acid carried along by the water vapor.

The concentrated solution of maleic acid collected at the bottom of the separator is next subjected to the dehydration stage, likewise carried out in a liquid-vapor cocurrent manner at a temperature of preferably between 140° and 160° C. at a pressure reduced to a value of preferably between 150 and 250 mm of mercury and with a residence time of preferably between 1 and 60 seconds.

The product obtained from the dehydration stage is next collected in a boiler. In this boiler the product is kept at a temperature of between 140° and 160° C.; a small amount of liquid phase containing residual deleterious by-product is continuously separated.

From the upper part of the boiler, steam and anhydride vapors are withdrawn. After being optionally superheated between about 160° and 170° C., the vapors are condensed in a first condenser where the condensed maleic anhydride is collected. The vapors escaping from this condenser then pass into at least one second condenser where they condense, yielding crude anhydride which is recycled with the concentrated acid to the dehydration stage. The gaseous phase escaping from the last condenser is scrubbed, the product of scrubbing being joined to that collected in the scrubber associated with the separator.

So as to provide a proportion of recycled anhydride of 15 to 35 parts by weight per 10 parts by weight of acid, in regulating the conditions of operation of the first condenser, production is limited to 10 parts of maleic anhydride produced per 3 to 33 parts of crude anhydride recycled. With the same object, one may add to the mixture being subjected to dehydration an added portion of stored anhydride resulting from the partial condensation of the oxidation product, in an amount which may go up to 1 part by weight per 1 part by weight of anhydride produced, preferably about 0.9 to 1.0 parts of finished stored anhydride to 1 part of anhydride produced.

The advantages of the present invention over a method employing the liquid-vapor countercurrent technique, and in particular with respect to a method employing agitated evaporators having a central rotor, are numerous.

On the one hand, the mechanical simplicity of the static cocurrent evaporator enables avoidance of: vibrations, the additional consumption of energy, the employment of lubricating oil and cooling liquid, as well as the risk of motor breakdown or of seizing of the rotor, leading to stoppage of the whole plant. Moreover, a minimal carry-over of maleic acid occurs at the outlet of the boiler associated with the dehydration evaporator, whereas in the employment of a countercurrent evaporator, there occurs a substantial carry-over of non-dehydrated maleic acid. In addition, under similar operating conditions, the heat exchange area required by a static coflow evaporator is less by 30% than that of a dynamic agitated counterflow evaporator. Furthermore, the volumetric flow per meter of wetted perimeter is about double for a coflow evaporator as compared to a counterflow. Moreover, the capacity of the coflow evaporator is from 1.3 to 1.4 times that of an agitated counterflow evaporator. (In this description, coflow and cocurrent are used interchangeably as is counterflow and countercurrent.) Thus, the employment of coflow static tubular evaporators leads to a more economical employment of the thermal fluids heating the evaporator tubes.

There are still further practical advantages of this invention insofar as the heat exchange area of a dynamic counterflow evaporator is limited by its construction, and on the market one finds only apparatus of this type of very specific dimensions, there being discontinuities between sizes. In contrast, in the case of a static coflow evaporator, any desired dimension can be realized; and as a function of the capacity desired for the plant, the dimensions of these evaporators can be calculated precisely by conventional methods and the evaporators can be manufactured accordingly with relative ease. Consequently, plants based upon such evaporators are much less costly than those based upon dynamic (agitated) counterflow evaporators. The economies not only involve the cost of the evaporators themselves, but also the necessary framework for placing them in position and their maintenance. (Heretofore, prejudicial to the use of static evaporators for the same function was the absence of the rotor with reduced clearance between its blades and evaporator wall. This system provides repartition and wiping of the liquid film, prevents important scale building by eventual scraping effect and limits liquid entrainment by the vapors in the counterflow pattern. The present invention shows that for the same function, the use of coflow static evaporators is advantageously possible assuming that initial liquid distribution on the inner wall of the tubes is correctly done.)

The preferred apparatus for conducting the invention comprises at least two thin-film evaporators arranged in series and is characterized in that:

the first thin-layer evaporator is of static tubular type and includes a feedpipe in the upper part and a discharge pipe in the lower part;

a separator is connected by its sidewall to the discharge pipe from the first evaporator and includes a first discharge pipe at the upper part and a second discharge pipe at the lower part;

the second thin-layer evaporator is of static tubular type, is connected to the second discharge pipe from the separator and includes a discharge pipe at the lower part.

In accordance with another aspect of the invention, the plant is characterized in addition in that:

a boiler connected to the lower part of the second evaporator, said boiler including a first discharge pipe at the lower part and a second discharge pipe at the upper part;

at least two condensers arranged in series and each comprising a discharge pipe for condensates, and also being connected serially on the one hand to the second discharge pipe from the boiler and on the other hand to a scrubber;

a recycle pipe for discharge of the condensates from the second condenser so as to join the second discharge pipe from the separator.

In this variant the boiler may either be connected to the second evaporator by a pipe or form with it only one single apparatus.

BRIEF DESCRIPTION OF THE DRAWINGS

The attached FIGURE is a schematic illustration of a preferred comprehensive embodiment of the invention.

DETAILED DESCRIPTION OF DRAWINGS

In the FIGURE, a first tubular static evaporator (1) includes firstly a feedpipe (2) at the upper part, connected in turn to a tank (not shown) containing the solution of maleic acid which is to be concentrated and dehydrated, and secondly a discharge pipe (3) at the lower part. A separator (4) connected by its sidewall to the pipe (3) includes a discharge pipe (5) for the vapors at the upper part and a discharge pipe (6) for the liquid at the lower part. A second tubular static evaporator (7) includes at the upper part a feedpipe (8) connected to the pipe (6) and is associated with a boiler (9) which comprises firstly a discharge pipe (10) at the upper part and secondly a discharge pipe (11) at the lower part. Two condensers (12) and (13) arranged in series are connected firstly to the boiler (9) by the pipe (10) and secondly to a scrubber (14) by a pipe (15). Each includes a pipe for discharge of the condensates (16) and (17). Pipe (24) recycles the condensates from the discharge pipe (17) to discharge pipe (6). A scrubber (18) is connected to the separator (4) by the pipe (5). Pipes (19) and (20) for putting the apparatus under vacuum are associated respectively with the scrubbers (14) and (18). In the pipe (17) is placed a reheater (22) and a pipe (21) is connected to it which is connected to a store of maleic anhydride. A reheater (23) appearing as a dotted line may be interposed in the pipe (10).

Each tubular evaporator or in the case of a multitubular evaporator, each tube of each evaporator, is preferably equipped with a liquid distributor which ensures correct wetting of the inner wall of the tube. This distributor advantageously consists of a metal cylinder which is placed in the upper portion of the tube and supported on it and the diameter of which is less than the inner diameter of the tube and which is equipped externally with one or more spiral turns. This distribution is a conventional one like that sold by LUWA-SMS and described in commercial booklets from their company.

The plant in accordance with the invention comprises in addition supply convention pipes for utilities (water, steam, thermal fluid) which are not shown in the FIGURE.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE

The continuous dehydration of maleic acid into maleic anhydride is carried out in a plant identical with that represented in the FIGURE.

The two evaporators include each 3 tubes, the total heat exchange area of each evaporator being 1.6 m$^2$. The inside and outside diameters of each tube are 40.9 and 44.9 mm.

A solution of maleic acid titrating 43% by weight and maintained at a temperature of 60° C. is introduced by way of the pipe (2) into the evaporator-concentrator (1). It is heated up to a temperature of 120° C. and at a pressure of 400 mm of mercury at a flow of 324.6 kg/h. The thermal fluid for heating the evaporator is saturated steam.

The product leaving the said evaporator is conducted through the pipe (3) into the separator (4). The concentrated maleic acid (90% by weight) flows through the pipe (6). Then there is added to it 250.4 kg/h of a mixture of maleic anhydride and acid containing 97.4% of anhydride as obtained from the condenser (13) through the pipe (17) and 111.8 kg/h of maleic anhydride of 97.8% purity obtained from stored finished product through the pipe (21).

The product thus composed of: 71.4% by weight of maleic anhydride, 25.9% by weight of maleic acid and 2.7% by weight of water is introduced through the pipe (8) into the evaporator-dehydrator (7) and brought to a temperature of 145° C. at a pressure reduced to 200 mm of mercury.

After dehydration in the evaporator (7), the product is collected in the boiler (9) where it is maintained at a temperature of 150° C. The residues are withdrawn through the pipe (11) at a flow of 10.7 kg/h and the vapors of anhydride and acid are withdrawn through the pipe (10). In the first condenser (12) the maleic anhydride produced is collected at a flow rate of 196.7 kg/h. This anhydride contains 1% by weight of maleic acid. Its content of water and fumaric acid is nil.

The preceeding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Apparatus for concentrating and dehydrating maleic acid to form maleic anhydride, comprising: at least first and second vertical, independent and distinct, falling thin-film, multitubular evaporators of the static type arranged in series, wherein the first thin-film multitubular evaporator of the static type has an upper part and a lower part and includes a feedpipe at the upper part and a discharge pipe at the lower part; a separator connected by its sidewall to the discharge pipe from the first evaporator and including a first discharge pipe at the upper portion thereof and a second discharge pipe at the lower part thereof, the second thin-film multitublar evaporator of the static type having a feedpipe having an upper part and a lower part connected to the second discharge pipe from the separator and including discharge means only at the lower part thereof; a boiler having an upper part and a lower part, said upper part of said boiler being connected to and in open communication with the lower part of the second evaporator, and said boiler further including a first discharge pipe for liquid at the lower part of the boiler and a second discharge pipe for vapor at the upper part of the boiler; a scrubber; condenser means having a pipe for discharge of the condensates, said condenser means being serially connected between the scrubber and the second discharge pipe from the boiler; and a recycle pipe connecting the discharge pipe from the condenser means with the second discharge pipe from the separator.

2. Apparatus according to claim 1, said condenser means having at least first and second condensers arranged in series, the second condenser being serially connected between the first condenser and the scrubber, said second condenser being equipped with a discharge pipe, and with the discharge pipe from the second condenser connecting with the recycle pipe to the second discharge pipe from the separator.

3. Apparatus according to claim 2, wherein a single housing contains said boiler and the second evaporator.

4. Apparatus according to claim 1, wherein a single housing contains said boiler and the second evaporator.

* * * * *